United States Patent
Kronmueller et al.

(10) Patent No.: US 10,413,740 B2
(45) Date of Patent: Sep. 17, 2019

(54) FEEDTHROUGH COMPONENT WITH STRUCTURED METAL COATING AND METHOD FOR PRODUCING SUCH A FEEDTHROUGH COMPONENT

(71) Applicant: BIOTRONIK SE & Co. KG, Berlin (DE)

(72) Inventors: Daniel Kronmueller, Nuremberg (DE); Hermann Kalb, Erlangen (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 15/583,084

(22) Filed: May 1, 2017

(65) Prior Publication Data
US 2017/0340890 A1    Nov. 30, 2017

(30) Foreign Application Priority Data
May 30, 2016    (DE) .................. 10 2016 109 898

(51) Int. Cl.
*A61N 1/37*    (2006.01)
*A61N 1/375*    (2006.01)

(52) U.S. Cl.
CPC .................. *A61N 1/3754* (2013.01)

(58) Field of Classification Search
CPC ....... A61N 1/3754; A61N 1/05; B23K 1/0008
See application file for complete search history.

(56) References Cited

U.S. PATENT DOCUMENTS

| | | | |
|---|---|---|---|
| 2005/0060003 A1 | 3/2005 | Taylor et al. | |
| 2007/0107524 A1* | 5/2007 | O'Brien | G01L 9/0073 73/754 |
| 2007/0269921 A1* | 11/2007 | You | B81C 1/00301 438/50 |
| 2007/0277374 A1 | 12/2007 | Suaning | |
| 2009/0007933 A1* | 1/2009 | Thomas | B08B 7/0042 134/1 |
| 2010/0258342 A1 | 10/2010 | Parker | |
| 2012/0138586 A1* | 6/2012 | Webster | A61B 18/20 219/121.64 |

(Continued)

FOREIGN PATENT DOCUMENTS

| | | |
|---|---|---|
| DE | 10 2014 204 528 A1 | 9/2015 |
| EP | 2 388 045 A1 | 11/2011 |

OTHER PUBLICATIONS

European Search Report and Annex to the European Search Report on European Patent No. 17 17 0832.4, dated Oct. 27, 2017 (8 pages).
(Continued)

*Primary Examiner* — Amanda K Hulbert
*Assistant Examiner* — Natasha Patel
(74) *Attorney, Agent, or Firm* — Buchanan Ingersoll & Rooney PC

(57) ABSTRACT

A method for producing a feedthrough component of a medical electronic device, in particular an implantable device, wherein a feedthrough main body, in particular made of ceramic, is produced and is provided over a large area with a metal coating, and the metal coating is then structured, wherein the structuring is performed by at least partially removing the metal coating in layers in a number of sub-steps by means of a processing laser.

17 Claims, 8 Drawing Sheets

(56) References Cited

U.S. PATENT DOCUMENTS

2014/0020951 A1* 1/2014 Shah .................... A61N 1/3754
174/667
2015/0045860 A1   2/2015 Markham et al.
2015/0157862 A1   6/2015 Greenberg et al.
2015/0250386 A1* 9/2015 Jose James ............ A61N 1/375
600/407
2017/0294322 A1* 10/2017 Morita .................. H01L 33/486

OTHER PUBLICATIONS

German Search Report for German Case No. DE 10 2016 109 898.1, dated Jan. 2, 2017 (7 pages).

* cited by examiner

FEEDTHROUGH COMPONENT WITH STRUCTURED METAL COATING AND METHOD FOR PRODUCING SUCH A FEEDTHROUGH COMPONENT

CROSS-REFERENCE TO RELATED APPLICATIONS

This patent application claims the benefit of and priority to co pending German Patent Application No. DE 10 2016 109 898.1, filed on May 30, 2016 in the German Patent Office, which is hereby incorporated by reference in its entirety.

TECHNICAL FIELD

The present invention present relates to a method for producing a feedthrough component of a medical electronic device, in particular an implantable device, wherein a feedthrough main body, in particular made of ceramic, is produced and is provided over a large area with a metal coating, and the metal coating is then structured. The present invention also relates to a feedthrough component which can be produced in particular by means of such a method.

BACKGROUND

Medical electronic devices which contain feedthrough components of this type have long been used on a mass scale, in particular as cardiac pacemakers, implantable cardioverters (especially defibrillators) or cochlear implants. The device could also be less complex, however, and for example could be constituted by an electrode lead or sensor lead.

Most implantable medical electronic devices of practical significance are intended to deliver electrical pulses to excitable body tissue via suitably placed electrodes. Many devices can also selectively measure signals of the nerve tissue in the patient's body and can record or evaluate said signals over a relatively long period of time in order to select individually tailored therapy and in order to monitor the success of the treatment in vivo. In order to perform this function, electronic/electrical function units for generating and regulating the pulses and for measuring stimuli are housed in the housing of the device. Electrodes or connections are provided externally on the device for at least one electrode lead, in the distal end portion of which the electrodes are attached to the tissue for pulse transmission.

For this purpose, an electrical connection must be established between the electrical and/or electronic components arranged in the housing interior and the respective electrode leads. This electrical connection is generally provided by means of a feedthrough and/or what is known as a header.

Here, a feedthrough of this type ensures at least one electrical connection between the interior of the housing and the exterior, and at the same time hermetically seals off the housing of the implant. The header fastened via the feedthrough guides the electrical connection of the feedthrough further to a contact point and serves for plugging the at least one electrode lead into a corresponding, usually standardized, socket. An electrical contact is thus produced between the implant and the connection piece of the electrode lead at the contact points of the socket. A feedthrough and a header can also be provided in a single component. In this case as well, a combined component of this type will be referred to hereinafter generally as a feedthrough.

The flange, which is required in order to hermetically seal the housing or implant with the feedthrough, usually consists of a metal (for example, titanium) or an alloy (for example, Ti-6Al-4V). It is advantageous to produce flange material and housing or implant material from materials of the same type so as to be able to join these to one another more easily in subsequent processes. The insulation body of the feedthrough consists substantially of a poorly conductive material (for example, insulation ceramic).

The contact elements penetrate through the insulation body and are electrically insulated from one another and with respect to the flange by means of the insulation body. The elements usually consist of highly conductive metals (for example, tantalum, niobium, titanium, platinum) or alloys (for example, PtIr, FeNi, 316L). Wire portions, or what are known as pins, are frequently used for the production of contact elements.

A great challenge is that of coordinating the different physical properties of the components and materials, in particular the coefficients of thermal expansion, with one another so that a sufficient seal can be ensured for the feedthrough over the intended service life.

When producing ceramic feedthroughs, the component parts (for example, insulation ceramics, flange, pins) are joined by means of a brazing process. In order to ensure the quality of the brazed connections in the case of feedthroughs of the aforementioned type, the respective insulation bodies are provided in part with a metal coating, which is intended to guarantee the brazing capability of the insulation body. The coating is an elemental metal (for example, tungsten, niobium, titanium) or an alloy. The coating is usually deposited on the insulation ceramic by means of a Physical Vapor Deposition (PVD) process and has a typical layer thickness of 1-20 μm.

It goes without saying that this metal coating can be provided merely in regions and must have a predefined structure, because the insulation ceramic of the feedthrough electrically separates two potentials from one another in a confined space (on the one hand the ground potential at the flange or housing, and on the other hand the signal potential at the pin). The separation of the potentials can be achieved by removing the coating again in part, or by applying no coating in part.

During the coating process, a sufficiently thick layer that is as homogeneous as possible must be ensured. However, in the case of the finished feedthrough component, the anticipated potentials must be prevented from being short-circuited, or the insulation resistance must be prevented from decreasing inadmissibly.

If a coating applied to the insulation ceramic is divided into areas by means of mechanical removal (for example, grinding, lapping), appropriate contours and dimensions must be provided already by the manufacturer of the insulation ceramic. During the decoating, the insulation ceramic is exposed to mechanical pressure and/or tensile loading, which stresses the product.

Alternatively, the coating can be structured by means of masks already during the application process. The masking process places high demands on the dimensional accuracy of the insulation ceramic and processing capability of the coating process. In order to obtain constant process results, the maskings and the insulation ceramics must match one another exactly in terms of dimension and tolerance, even with different batch sizes and over a number of processes. As a result of the coating, the masks lose their dimensional accuracy and must be reworked or replaced.

The masks must rest very closely around the insulation ceramics, since otherwise coating is also applied behind the mask. If the masks rest on the insulation ceramics in an irregular manner, this leads to an irregular coating edge and thus inevitably also to deviations in the electrical properties (for example, capacitance, inductance) of the insulation ceramics and, thus, also to batch deviations of the feedthrough and the medical device. The masks used during the process themselves cast shadows and thus reduce the deposition rate on the insulation ceramics to be coated. Furthermore, irregular transitions between the coating and masked region lead to visual anomalies on the product or lead to problems in subsequent processes, and therefore are undesirable.

The mechanical fitting and removal of the masks is subject to very high demands on the repeatability of handling systems (robots, linear axes, camera systems). In the event of improper handling, the insulation ceramic or coating thereof can be destroyed (for example, scratched, abraded).

Very small structures over a number of layers can be produced only by means of a multi-stage process or by means of photolithography. For photolithography, the insulation ceramic is coated partially or wholly with a photoresist. This is exposed, and developed as appropriate. The remaining photoresist layer is removed and serves as a masking, which can be stripped again from the component after the coating process.

The present invention is directed toward overcoming one or more of the above-identified problems.

SUMMARY

An object of the present invention is to specify an improved method of the type in question, which method in particular provides a feedthrough component having advantageous, clearly defined electrical properties, in particular in such a way that the insulation properties of the feedthrough can be selectively adjusted. The component preferably can also be provided so as to be particularly compact and/or should allow the inclusion of a large number of connection elements having high functional reliability.

At least this object is achieved by a method having the features of claim 1. Expedient developments of the method are the subject of the dependent method claims. A novel feedthrough component having the features of claim 12 is also proposed. Expedient developments of the proposed feedthrough component are the subject of the dependent product claims.

The present invention comprises the concept of departing both from the known methods with preliminary structuring of a metal coating already at the time of application of said coating, and also from the methods with mechanical structuring of a metal coating applied beforehand over a large area. The present invention also comprises the concept of using a method, instead of those above, in which the metal coating applied beforehand over a large area is structured and/or modified by means of a laser processing method. On the whole, it is proposed in accordance with the present invention that the structuring is performed by at least partial removal of the metal coating in layers in a number of sub-steps by means of a processing laser.

With the method according to the present invention, at least one of following advantages can be attained, and in preferred embodiments a combination of a number of these advantages:

The high-temperature brazing process is subject to few fluctuations. The yield of the process is increased by an improved quality of the intermediate products.

The properties of the feedthroughs, in particular the electrical properties, can be selectively set or manipulated already on the semifinished product. A selectively post-processed surface can reduce the variation of the process results from the coating operation.

Materials that have deviating coefficients of thermal expansion can be processed. The materials no longer necessarily have to be coordinated with one another so that the thermal loading does not lead to cracks and warping.

The path of the brazing solder during the joining process can be interrupted, controlled and manipulated by means of expansion joints and structural design.

Large metallization areas can be replaced by a multiplicity of smaller geometries of identical area.

Covering caps or maskings no longer have to be produced and managed.

In one embodiment of the inventive method, different, step-specific operating parameters of the processing laser are adjusted at least in some sub-steps. This is the case, in particular, when the metal coating comprises sub-layers of different composition and/or different thickness and/or different position relative to a reference plane (for example, the plane of a workpiece table) or if different aspects of the structuring to be performed are provided in the sub-steps.

In a currently preferred method sequence, contours of the feedthrough main body and/or the metal coating are scanned using a scanner, and the position of the processing laser is controlled by means of the scanner. Such tool control by means of workpiece scanning by a scanner (and a comparison with stored workpiece geometries and processing parameters) is known per se, and therefore no further explanation is required here for a person skilled in the art.

In one embodiment of the mentioned variant, the situation is mastered that a smaller thickness is provided or the metal coating is locally interrupted in an edge region of a partial metal coating or in a step edge region of a metal coating of stepped thickness. The processing laser is then controlled in such a way that the edge region or step edge region of smaller thickness or with interruptions is modified. This is implemented in such a way that the edge or step edge obtains a predefined contour and/or substantially the same thickness as the corresponding middle region of the metal coating or obtains a thickness that decreases with a predefined course.

In a further embodiment, in the case of a removal of the metal coating over the entire thickness, a surface layer of the feedthrough main body is also removed at the same time. In particular, the focal plane of the processing laser for this purpose, at least in a final removal step, is set below the boundary between the metal coating and feedthrough main body.

In another embodiment, the structuring comprises a local or regional thickness reduction of the metal coating at the surface. The metal coating in this embodiment, which can be combined with the aforementioned embodiment, is thus not removed in the corresponding regions as far as the insulation ceramic, and instead is merely thinned or levelled (in the case of a coating previously of irregular thickness).

In another embodiment, the structuring comprises a local or regional increase in the thickness of the metal coating. This is achieved by melting the metal coating in portions and/or in layers and displacing the melted portions during the scanning of the feedthrough component with the processing laser. In an embodiment of practical significance, at least one edge region of the metal coating is provided here with an increased thickness. A levelling of uneven layer surfaces can also be provided.

In a further embodiment, different focal planes can be set locally or regionally during the structuring process in order to structure a metal coating provided at different heights of the feedthrough main body.

In accordance with a relatively independent aspect of the present invention, the metal coating of a novel feedthrough component has a structure that is impressed subsequently by local melting and evaporation of metal of the metal coating. A feedthrough component of this type can be formed advantageously by means of the method explained above, however, the provision of said component is not necessarily bound to the application of this method.

In one embodiment, the impressed structure also has regions in which material of the feed-through main body is removed at the surface.

In further embodiments, the thickness of the structured metal coating in edge regions is increased compared to middle regions or decreases with a predefined gradient of progression and/or is provided with a predefined contour.

In further embodiments of the proposed feedthrough component, at least one expansion joint is formed within the metal coating in order to compensate for different coefficients of thermal expansion of the feedthrough main body and the metal coating. This embodiment advantageously enables a component construction in which functional disruptions of the feedthrough as a result of frequent alternating thermal load are largely ruled out.

Further embodiments of the present invention could be learned from the following description, in combination with the Figures, and/or the dependent claims.

DESCRIPTION OF THE DRAWINGS

Advantages and expedient features of the present invention will also become clear from the following description of an exemplary embodiment with reference to the drawings, in which.

DETAILED DESCRIPTION

Figure 1:
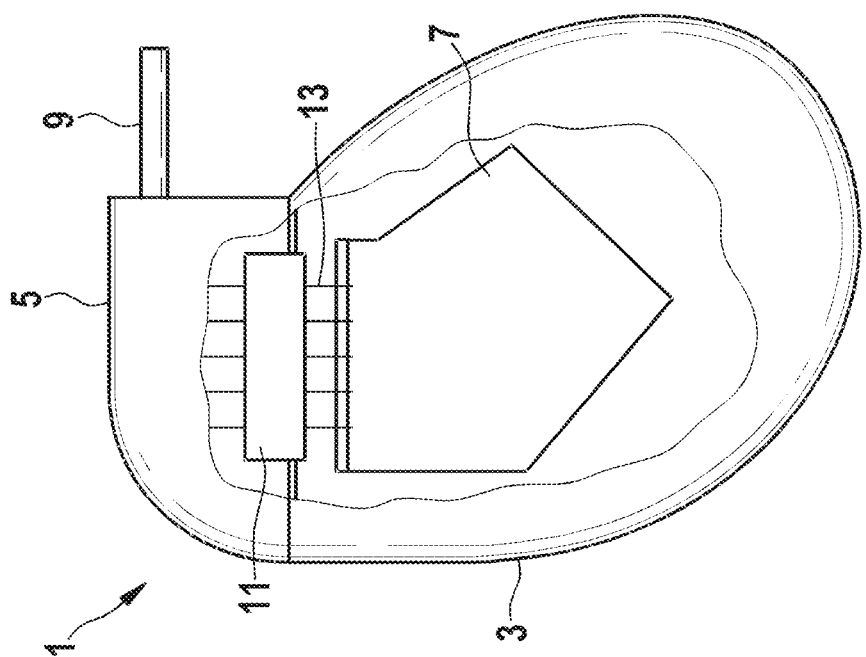
FIG. 1 shows a schematic, partly cut-away illustration of an implantable medical electronic device.

FIG. 1 shows a cardiac pacemaker 1 with a pacemaker housing 3 and a header 5, in the interior of which, in addition to other electronic components, there is arranged a printed circuit board (PCB) 7, with an electrode lead 9 connected to the lead connection (not shown) arranged in the header 5. A feedthrough 11 provided between the device housing 3 and header 5 comprises a plurality of connection pins 13. The connection pins 13 are plugged at one end through a corresponding borehole in the printed circuit board 7 and are soldered thereto.

Figure 2:
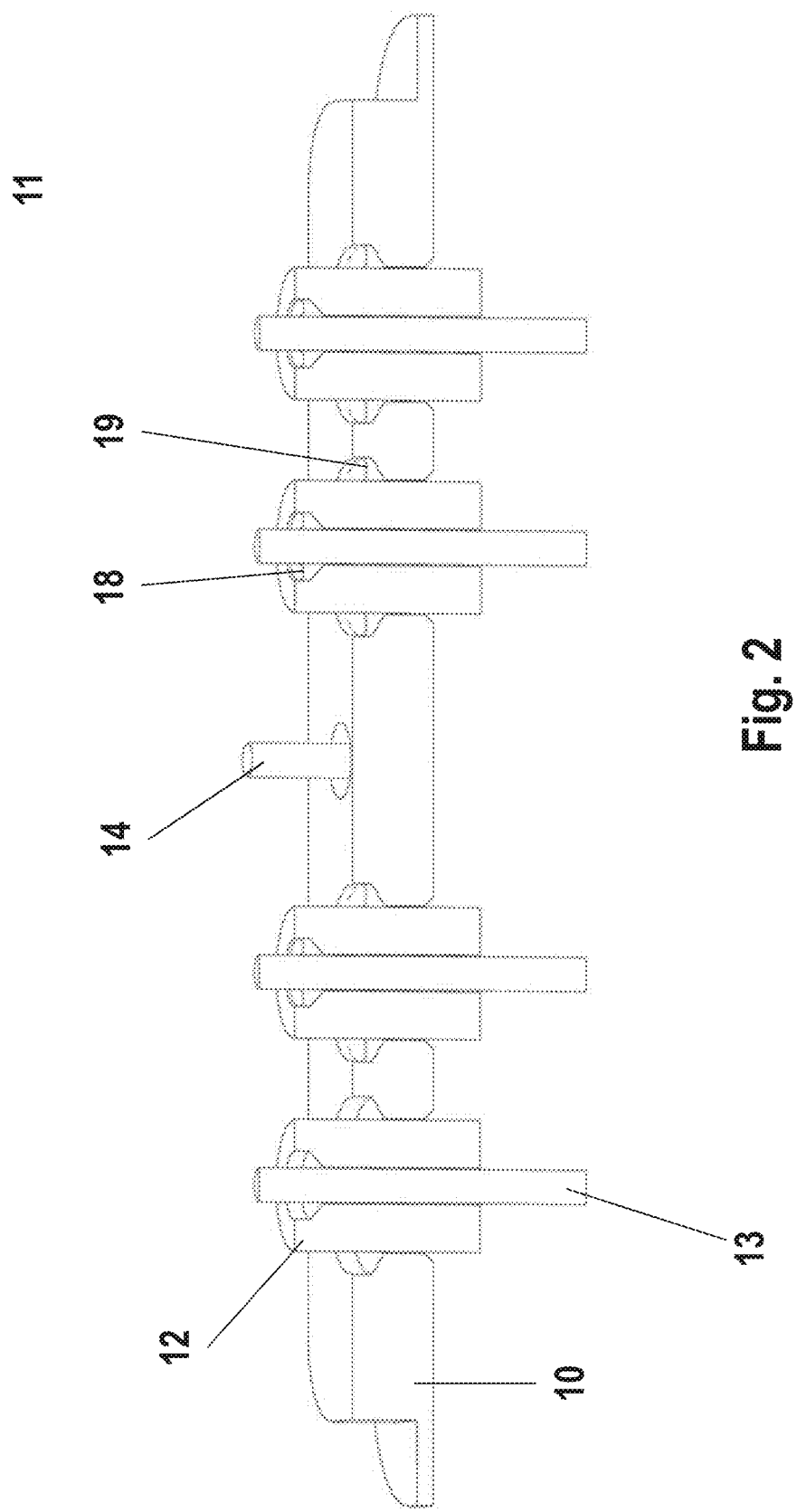
FIG. 2 shows an exemplary embodiment of a feedthrough component produced in accordance with the present invention in the form of a longitudinally cut, perspective view.

FIG. 2 shows an electrical feedthrough 11 consisting of a flange 10, insulation ceramics 12, signal pins 13, and a grounding pin 14. The signal pins 13 are each joined into the insulation ceramic 12 by means of a brazing solder 18, and the insulation ceramic 12 is joined similarly into the flange by means of a brazing solder 19. The grounding pin 14 is usually also contacted with the flange by means of a brazing solder.

Figure 3:
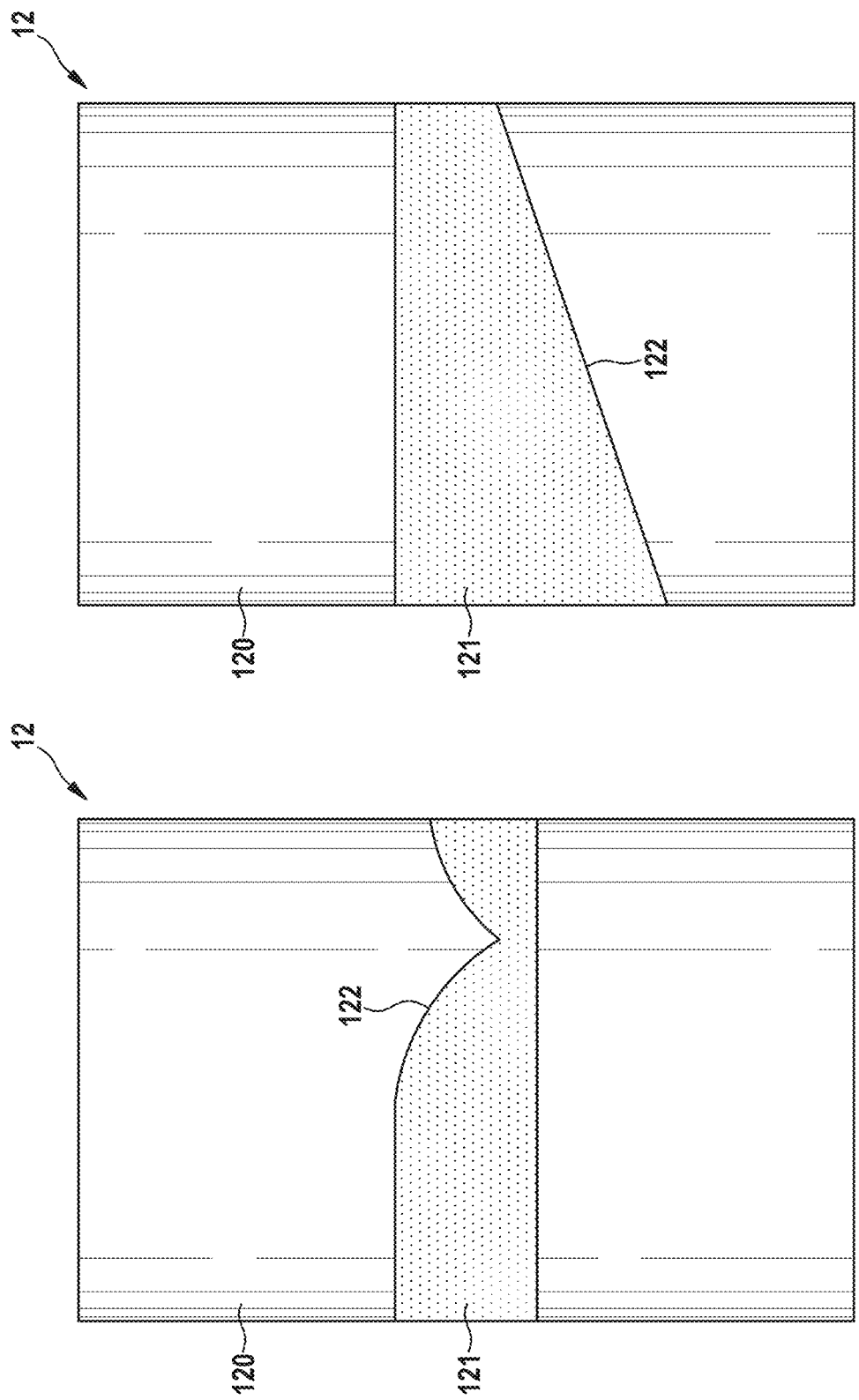
FIG. 3 shows two schematic illustrations of coated insulation ceramics of an electrical feedthrough.

FIG. 3 is a schematic illustration of two coated insulation ceramics 12 of an electrical feedthrough. The insulation ceramics 12 consist of ceramic substrate 120 and a metallization 121. The metallization 121 can be applied by means of a PVD process. Coating defects 121 can form during the PVD process and are caused as a result of said process. Said defects lead to a modified coating area and therefore to irregular results during the brazing process of the medical feedthrough.

Figure 4:
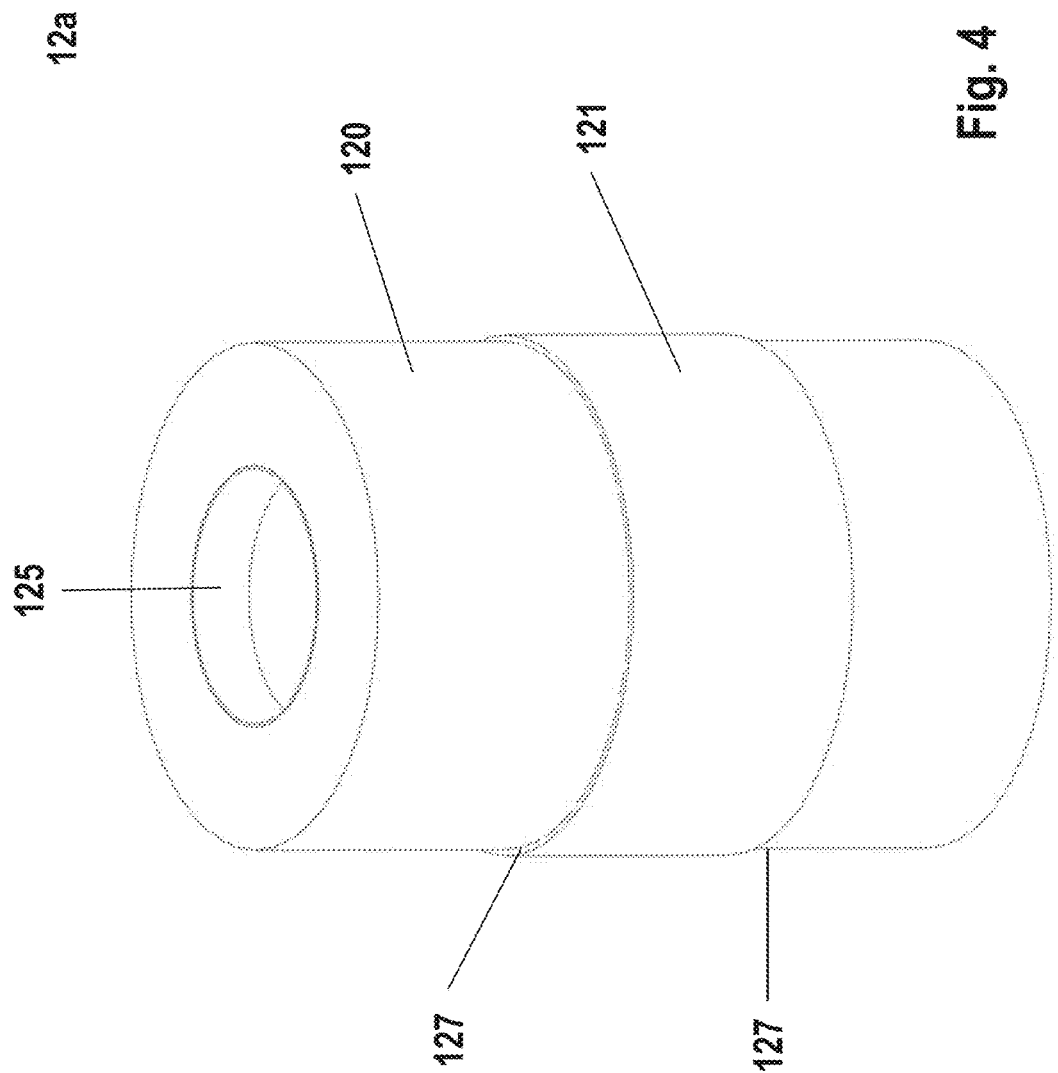
FIG. 4 shows a perspective illustration of a further coated insulation ceramic.

FIG. 4 is a schematic illustration of a coated insulation ceramic 12a. A metallization 121 has been applied to the ceramic substrate 120. In order to achieve a sharp delimitation of the metallization 121, a decoating 127 has been performed peripherally at each of the edges of the metallization 121. By means of the decoating 127, the area of the coating is reduced, but a high-contrast, sharply delimited transition between the ceramic and the coating is achieved. The height of the step can be adjusted both by the number and density of laser pulses on the metallization 121 and by the number and density of the laser pulses on the ceramic substrate 120.

Figure 5:
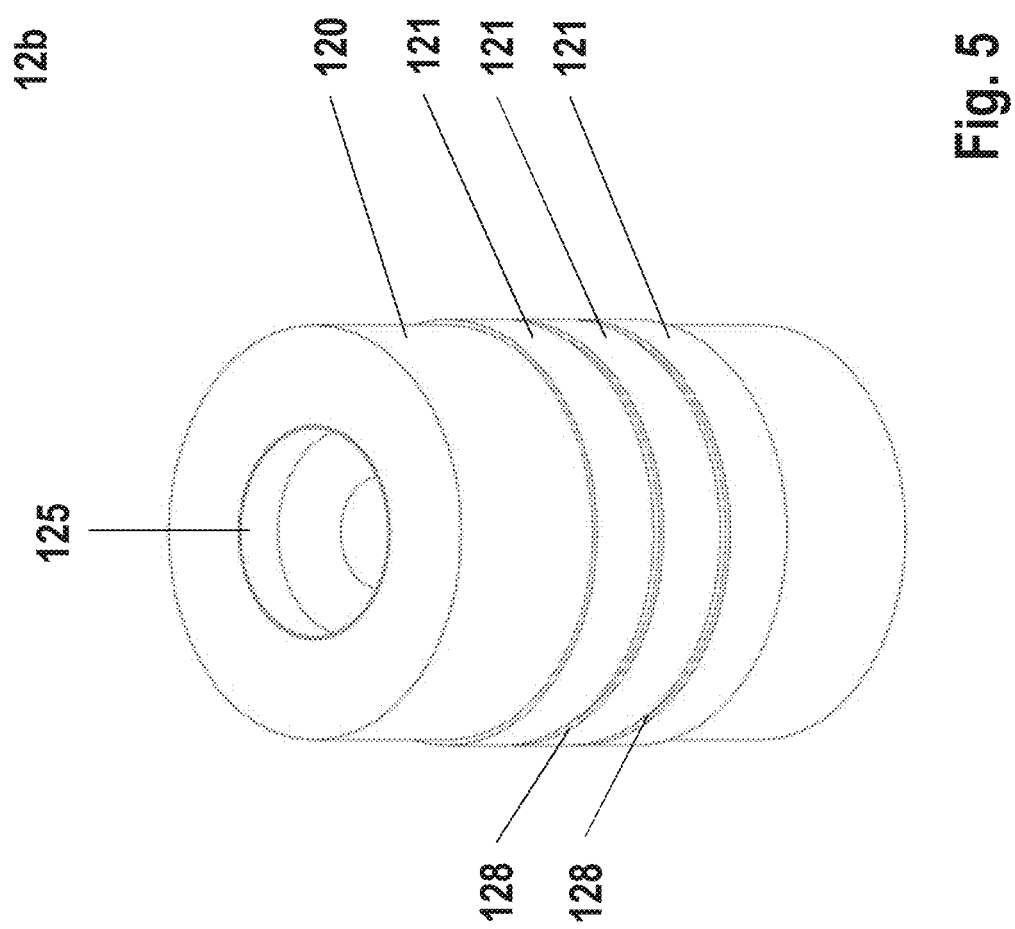
FIG. 5 shows a perspective illustration of a further coated insulation ceramic.

FIG. 5 is a schematic illustration of a coated insulation ceramic 12b. A metallization 121 has been applied to the ceramic substrate 120. In order to avoid the risk of cracks in the metallization 121 on account of stresses, the metallization 121 is interrupted by joins 128. The depth of infiltration into the metallization or into the ceramic substrate can be adjusted by the number and density of the laser pulses.

Figure 6:
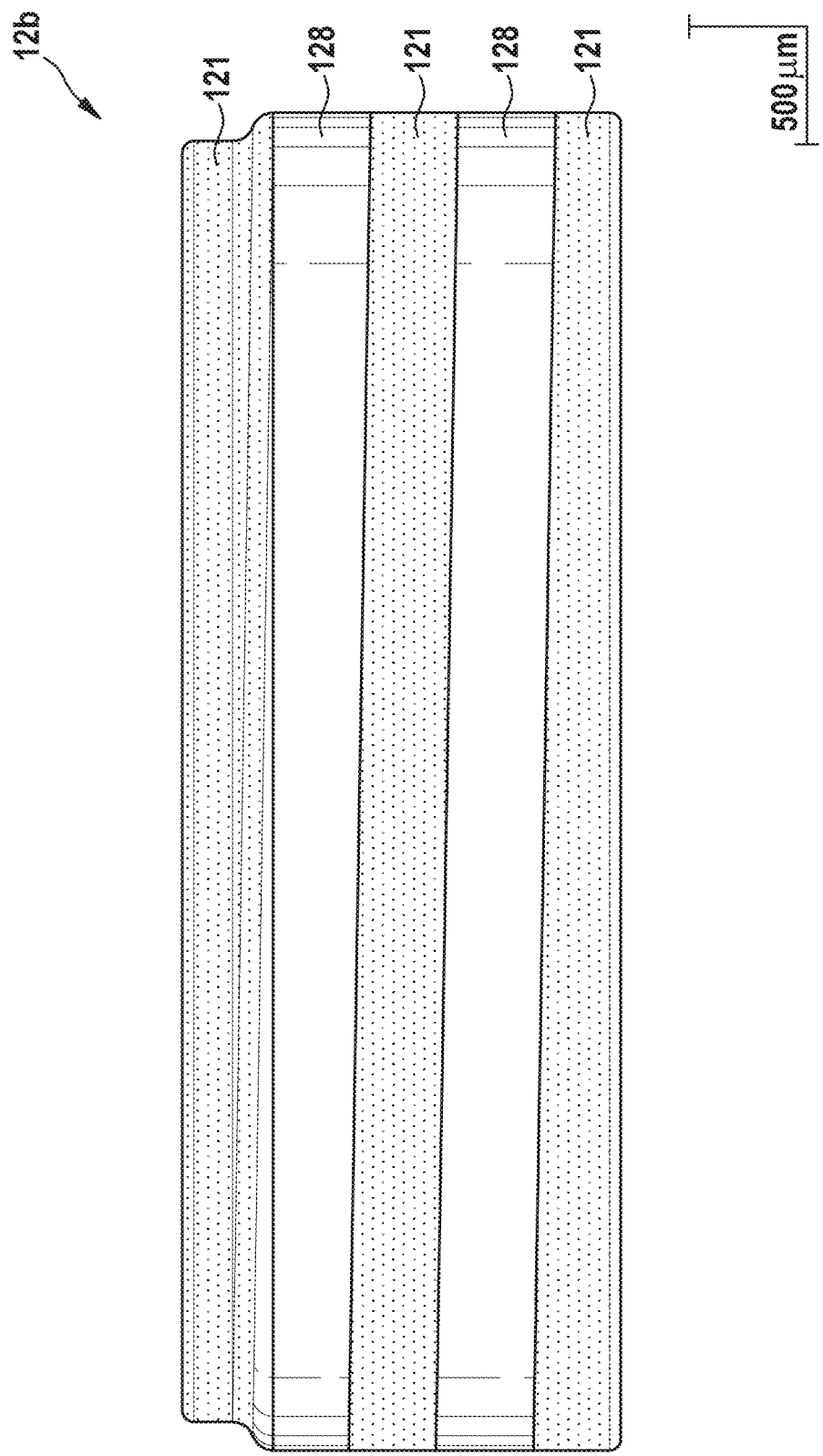
FIG. 6 shows a schematic illustration of a further coated insulation ceramic.

FIG. 6 is a schematic illustration of a coated insulation ceramic. The metallization 121 is interrupted by joins 128.

Figure 7:
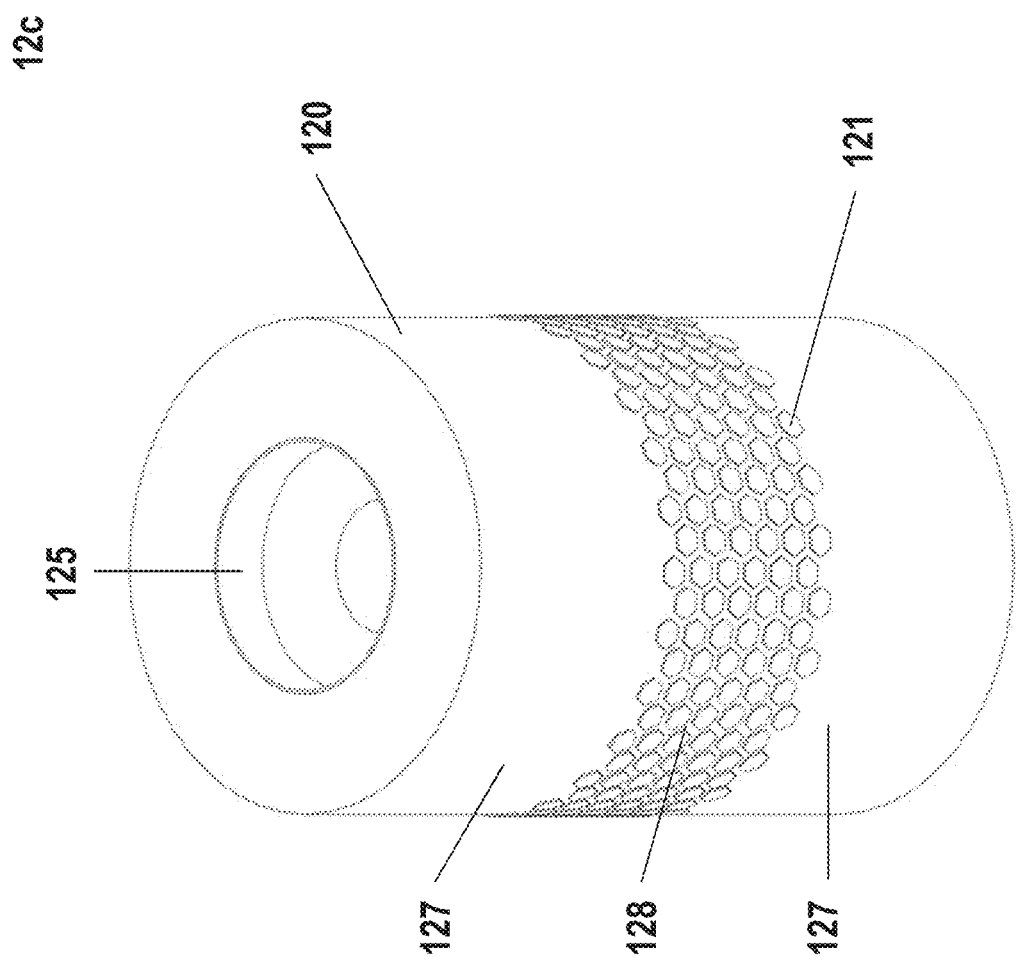
FIG. 7 shows a further perspective illustration of a coated insulation ceramic.

FIG. 7 is a schematic illustration of a coated insulation ceramic 12. A metallization is applied to the lateral surface side of the ceramic substrate. By means of a decoating 127 of the areas not required, the ceramic substrate is exposed. The remaining coating is exposed and structured by a plurality of joins 128. The remaining metallization 121 is composed of a multiplicity of individual areas.

Figure 8:
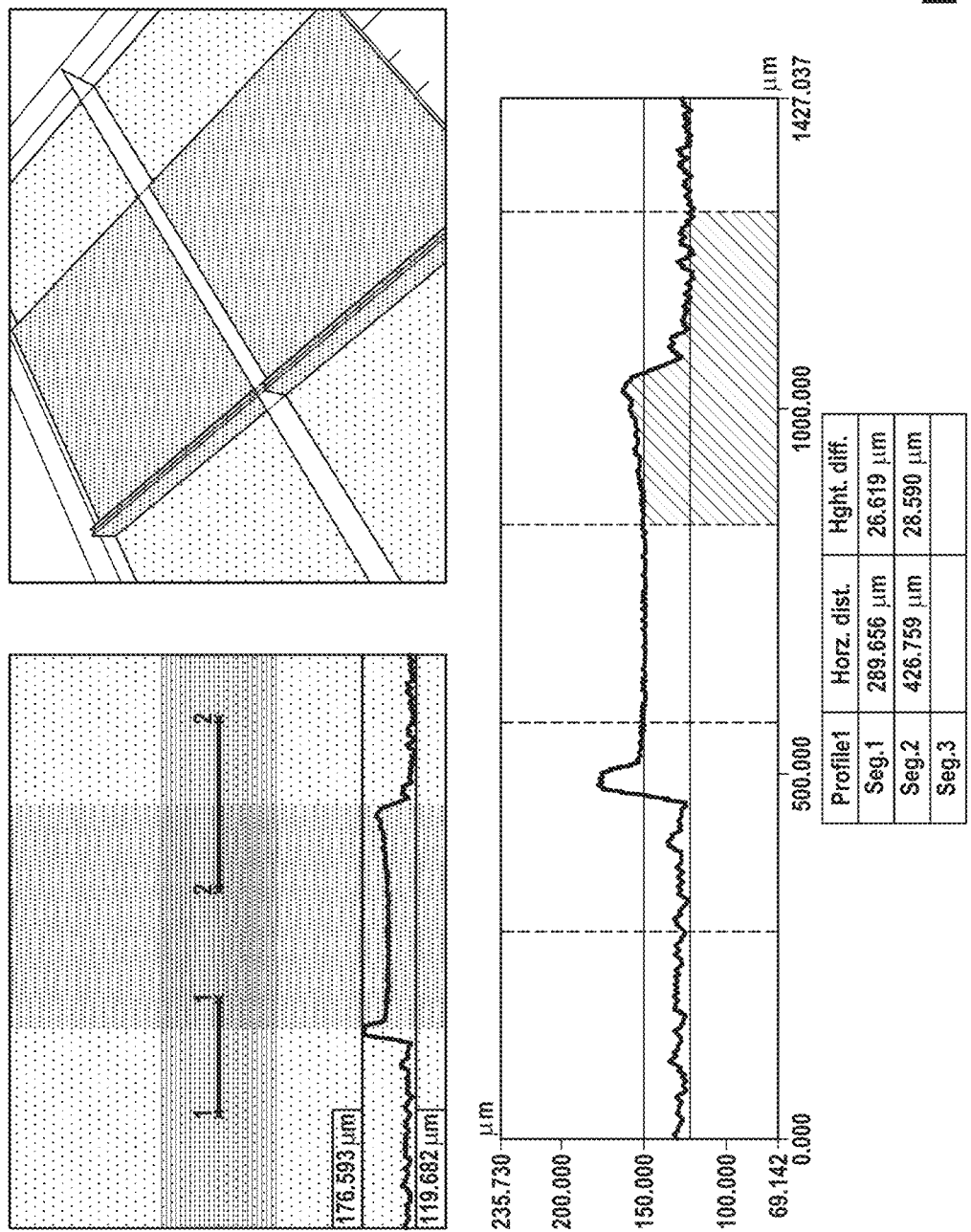
FIG. 8 shows illustrations and a depth profile for clarifying the geometrical characteristics of an exemplary embodiment of an insulation ceramic coated in accordance with the present invention.

FIG. 8 shows the depth profile on an insulation ceramic. What was measured was the height difference between the metallization 121 and two decoated areas 127. The metallization thickness on the substrate is 12 μm±3 μm. For complete decoating, approximately 15 μm±3 μm must be lasered into the ceramic in layers. The roughness of the decoated substrate is greater than that of the untreated ceramic.

What can be clearly seen is the heightening on the left-hand side of the metallization 121. It was produced by repeated decoating of the left-hand region from left to right.

Embodiments of the proposed method can comprise the following aspects, in particular:

The insulation ceramic is coated partially or wholly with at least one metallization or an alloy. Biocompatible metals (for example, Nb, Ti, Wo) are preferably used. Metals of which the coefficient of thermal expansion lies close to that of the ceramic substrate are advantageous.

It can be advantageous to construct the metallization from a number of layers. The typical layer thickness of the metallization is a few micrometers.

After the coating, this is removed from the insulation ceramic in layers by means of a laser beam. For this purpose, a laser beam scans the coated ceramic and in so doing the metallization is removed from the ceramic partially or wholly. A conventional marking laser in pulse operation (for example, a fiber laser) is suitable for this purpose. The laser is aligned with the component by means of a scanner. This positions the laser and steers the focus in a number of axes over the component.

The coating can be removed partially or wholly by means of the laser. The coating can also be microstructured in part or over the entire area. It is advantageous to produce areas of different thickness in the metallization so as to be able to better control the dissolution rate in the brazing solder.

In the case of coating materials that have a coefficient of thermal expansion deviating from that of the substrate, it can also be advantageous to incorporate defined parting lines in the coating, which prevent the layer from tearing off or detaching in an uncontrolled manner during the brazing process.

It can be advantageous to subsequently process the typical transition zones of the PVD masking process with a slowly tapering-off coating thickness and/or irregular edges, such that defined material transitions are produced.

It is also advantageous to structure the metallization on the insulation ceramic, in part, in portions, or over the entire area, in order to positively improve the electrical properties of the feedthrough or the result of the subsequent brazing process.

The repeatability of economical laser scanner systems lies typically at several 0.001 mm, and the depth of focus of the laser scanner is a few millimeters, such that the decoating or post-processing provides much better results compared to a conventional masking process.

Since, when removing the coating by means of a laser, contaminants can form on the surrounding material, it can be advantageous to remove the coating a few focal planes (typically 1×-10×) deeper into the substrate, such that the metallization and vaporization or splashes thereof can be removed without leaving behind any residue.

Homogenization

By selective ablation of the layer using a fiber or ultra-short pulse laser (USPL), the layer thickness of the coating can be reduced or locally increased. Due to the selective reworking of the layer thickness, small defects in the coating can be compensated, and irregularities in the coating can be removed. A uniform homogeneous cell structure or line structure with an adjustable defined remaining unevenness can be produced on the component by the scanning of the entire coating in a defined focal plane.

Edge Contrast

When coating by means of PVD methods by means of a mask process, the coating may taper off to an irregular extent as a result of the process. The transition region is typically a few μm depending on the quality of the masks and coating thickness, and can be arranged offset to the outer edges of the insulation ceramic.

By selective post-processing with the laser, the gradient between the areas can be increased, and the transition zone can be eliminated. The area bordering the coating is scanned with the laser and any impurities or residues present are removed in layers. In order to yet further increase the contrast, it is advantageous to also expose the base material in the coating region in addition to the region bordering the coating and to sublime a few μm of the ceramic.

The remaining coating region is thus delimited very clearly and in a highly contrasting manner from the ceramic. In addition to the visual difference on account of the material, the height difference between coating and insulation ceramic can thus be intensified. The coating region can be identified more reliably manually or during an automatic visual inspection.

It can be advantageous to form the edges between the coating and the insulation ceramic not as a straight line, but instead with a predefined regular contour.

It can be advantageous to produce a transition zone with a defined gradient. For this purpose, the layer thickness in the region of a lead-out or lead-in zone is selectively reduced, such that a defined soft edge contrast is produced.

Layer Heightening

By melting and clearing a larger area by means of a pulsed laser, the layer thickness can also be locally heightened.

For this purpose, the coated insulation ceramic is scanned by the laser and the coating is melted in layers. By clever selection of the laser parameters, part of the melted coating can be displaced into the feed direction of the beam, where it cools.

It is advantageous to heighten the coating at the edge so as to attain a clear contrast for visual checks. It may also be advantageous to produce a local heightening in order to compensate the removal by the dissolution of the coating in the brazing solder.

Expansion Joints

The insulation ceramic and the coating consist of different materials and have different coefficients of thermal expansion. For large or continuous areas, it is therefore technically necessary to choose materials having at least similar coefficients of expansion in order to reduce or to minimize the risk of uncontrolled layer detachment or layer tearing during or after the joining process. Due to the insertion of an expansion joint (controlled separation of coating and insulation ceramic) at defined regions, the risk of uncontrolled layer detachment, layer shifting, or layer tearing during the brazing process can be restricted. Since the expansion joints prevent a heat crack between coating and insulation ceramic from spreading uncontrollably in the material on account of different coefficients of thermal expansion, it is possible to also use material pairings having different coefficients of thermal expansion.

Due to the expansion joints, material warping on the coating, in particular in the case of multi-metal layer systems, is avoided.

Combined or Segmented Areas

Due to the structuring of the coated area, the coating of the lateral surface can be divided into small areas. Instead of a large continuous coating, the coating can be composed of a number of small individual areas. The risk of cracks in the coating on account of the different thermal expansion can thus be minimized.

The brazing solder (for example, gold), which later flows into the gap between ceramic and flange, continues to reliably join the individual component parts so as to form a hermetically tight component. The structurings are bridged by the surface tension of the liquid solder.

It may be advantageous if the direction of the structuring lies perpendicularly to the direction of flow of the solder so as to prevent this from flowing through the soldering gap. However, it can also be advantageous if the direction of the structuring lies in the direction of the flow of solder so as to promote a flow of the solder into the soldering gap.

It can be advantageous to extend the effective path through the soldering gap by means of a combined or segmented area.

Fine Tuning

In order to keep the deviation of the product properties as low as possible, it is necessary to manufacture the insulation ceramic with electrical properties and manufacturing tolerances that are as constant as possible. Since the coating region produces a direct influence on the electrical properties and on the process stability of the brazing process, it is important to be able to set these so as to be reproducible to the greatest possible extent.

For the rest, the present invention can also be embodied in a large number of modifications of the examples shown here and aspects of the present invention highlighted further above.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:

1. A method for producing a feedthrough component of a medical electronic device comprising:
   providing a feedthrough main body made of ceramic;
   providing a metal coating over a large area of the feedthrough main body; and
   structuring the metal coating, wherein the structuring is performed by at least partially removing the metal coating in layers in a number of sub-steps using a laser.

2. The method according to claim 1, wherein different, step-specific operating parameters of the processing laser are adjusted at least in some of the sub-steps.

3. The method according to claim 1, wherein contours of the feedthrough main body and/or the metal coating are scanned by a scanner and the position of the processing laser is controlled by the scanner.

4. The method according to claim 1, wherein the metal coating has a different thickness in regions, and operating parameters of the processing laser when scanning the metal coating are adjusted depending on the local thickness.

5. The method according to claim 4, wherein a smaller thickness is provided or the metal coating is locally interrupted in an edge region of a partial metal coating or in a step edge region of a metal coating with a stepped thickness, and the processing laser is controlled in such a way that the edge region or step edge region with smaller thickness or with interruptions is modified in such a way that the edge or step edge obtains a predefined contour and/or substantially the same thickness as the corresponding middle region of the metal coating or obtains a thickness that decreases with a predefined course.

6. The method according to claim 1, wherein in the case of a removal of the metal coating over its entire thickness, a surface layer of the feedthrough main body is also removed at the same time.

7. The method according to claim 6, wherein the focal plane of the processing laser, at least in a last removal step, is set below the boundary between the metal coating and feedthrough main body.

8. The method according to claim 1, wherein the structuring comprises a local or regional thickness reduction of the metal coating at the surface.

9. The method according to claim 1, wherein the structuring comprises a local or regional increase in thickness of the metal coating, which is caused by melting the metal coating in portions and/or in layers and displacing the melted portions during the scanning of the feedthrough component with the processing laser.

10. The method according to claim 9, wherein at least one edge region of the metal coating is provided with an increased thickness.

11. The method according to claim 1, wherein different focal planes are set locally or regionally during the structuring process in order to structure a metal coating provided at different heights of the feedthrough main body.

12. The method according to claim 1, wherein the feedthrough main body is joined with a flange and/or a signal pin by means of a brazing solder.

13. A feedthrough component of a medical electronic device, in particular an implantable device, which has a feedthrough main body, in particular made of ceramic, which is provided over a large area with a structured metal coating, which in particular is a multi-layered coating, in particular produced in accordance with claim 1, wherein the metal coating has a structure impressed subsequently by local melting and/or evaporation of metal of the metal coating.

14. The feedthrough component according to claim 13, wherein the impressed structure also has regions in which material of the feedthrough main body is removed at the surface.

15. The feedthrough component according to claim 13, wherein the thickness of the structured metal coating in edge regions is increased compared to middle regions or decreases with a predefined gradient of progression and/or is provided with a predefined contour.

16. The feedthrough component according to claim 13, wherein at least one expansion joint is formed within the metal coating in order to compensate for different coefficients of thermal expansion of the feedthrough main body and the metal coating.

17. The feedthrough component according to claim 13, wherein the feedthrough main body is joined with a flange and/or a signal pin by means of a brazing solder.

* * * * *